(12) United States Patent
Mihashi et al.

(10) Patent No.: US 6,802,609 B2
(45) Date of Patent: Oct. 12, 2004

(54) EYE CHARACTERISTIC MEASURING APPARATUS

(75) Inventors: Toshifumi Mihashi, Tokyo (JP); Yoko Hirohara, Tokyo (JP)

(73) Assignee: Kabushiki Kaisha TOPCON (JP)

( * ) Notice: Subject to any disclaimer, the term of this patent is extended or adjusted under 35 U.S.C. 154(b) by 378 days.

(21) Appl. No.: 09/851,729

(22) Filed: May 9, 2001

(65) Prior Publication Data

US 2002/0041359 A1 Apr. 11, 2002

(30) Foreign Application Priority Data

May 12, 2000 (JP) ........................................ 2000-141032

(51) Int. Cl.[7] .................................................. A61B 3/10
(52) U.S. Cl. ...................................................... 351/221
(58) Field of Search ............................... 351/200, 205, 351/206, 212, 221, 246, 213, 211

(56) References Cited

U.S. PATENT DOCUMENTS

| 5,042,938 | A | * | 8/1991 | Shimozono | 351/205 |
| 5,206,672 | A | * | 4/1993 | Rowe | 351/205 |
| 5,347,327 | A | * | 9/1994 | Sekine et al. | 351/205 |
| 5,521,657 | A | * | 5/1996 | Klopotek | 351/246 |
| 5,777,719 | A | * | 7/1998 | Williams et al. | 351/212 |
| 5,929,970 | A | * | 7/1999 | Mihashi | 351/246 |
| 6,042,233 | A | * | 3/2000 | Mihashi et al. | 351/221 |
| 6,050,687 | A | * | 4/2000 | Bille et al. | 351/212 |
| 6,070,981 | A | * | 6/2000 | Mihashi et al. | 351/212 |

* cited by examiner

Primary Examiner—Marvin M. Lateef
Assistant Examiner—John R. Sanders
(74) Attorney, Agent, or Firm—Baker Botts LLP

(57) ABSTRACT

The invention includes an eye characteristic measuring apparatus which achieves accurate measurement by taking a difference component with relation with measured data in a reference optical path when optical characteristics of an eye are measured. Specifically the measuring apparatus is provided with a reference optical system separate from a light receiving system. Measurement of eye characteristics can include both aberration of an eye and aberration in the measuring apparatus. In order to achieve high accuracy, the eye characteristic measuring apparatus of the invention substantially removes aberration in strain of the equipment produced after the initial stage and aberration of the equipment caused by deformation due to temperature.

13 Claims, 11 Drawing Sheets

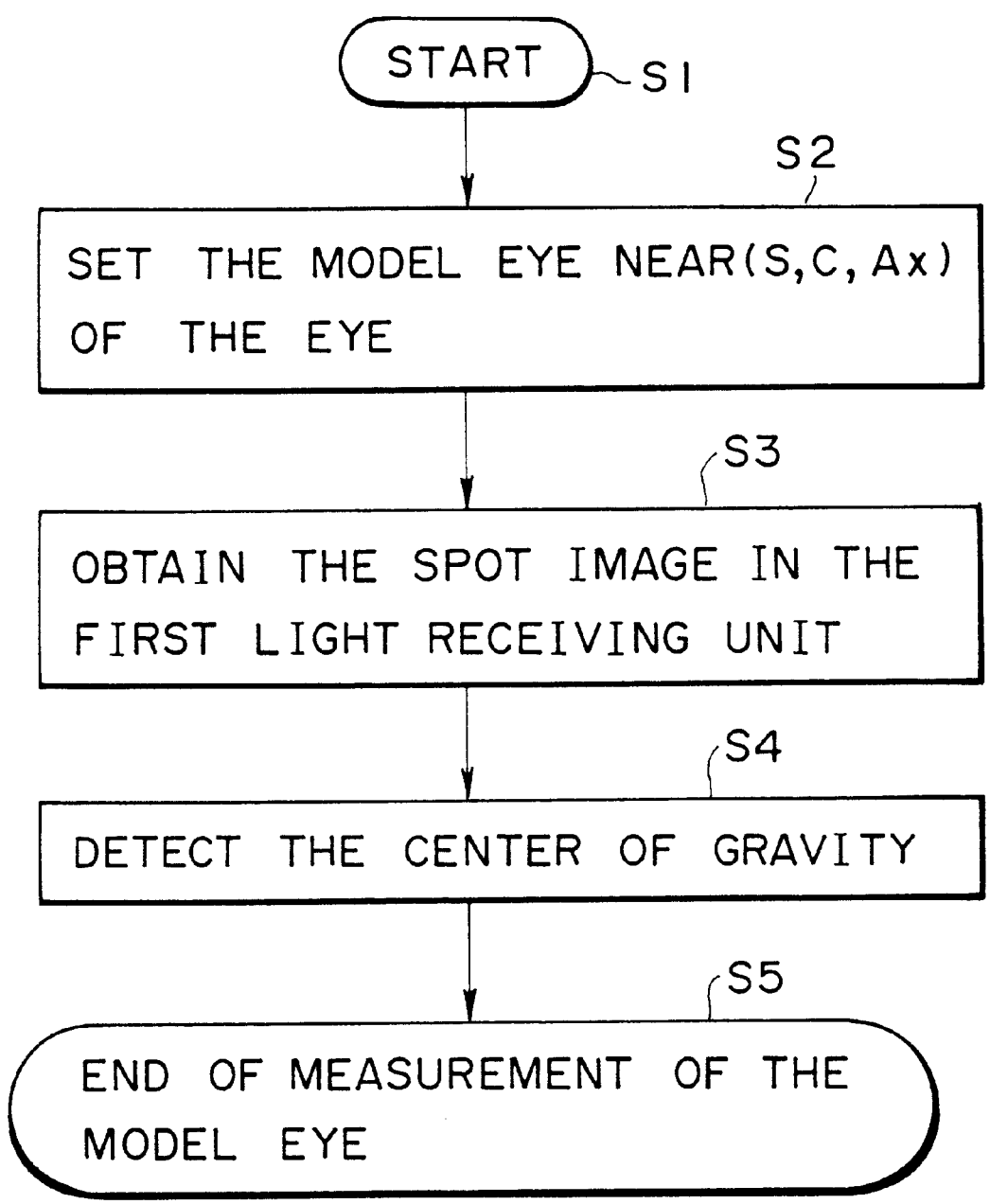

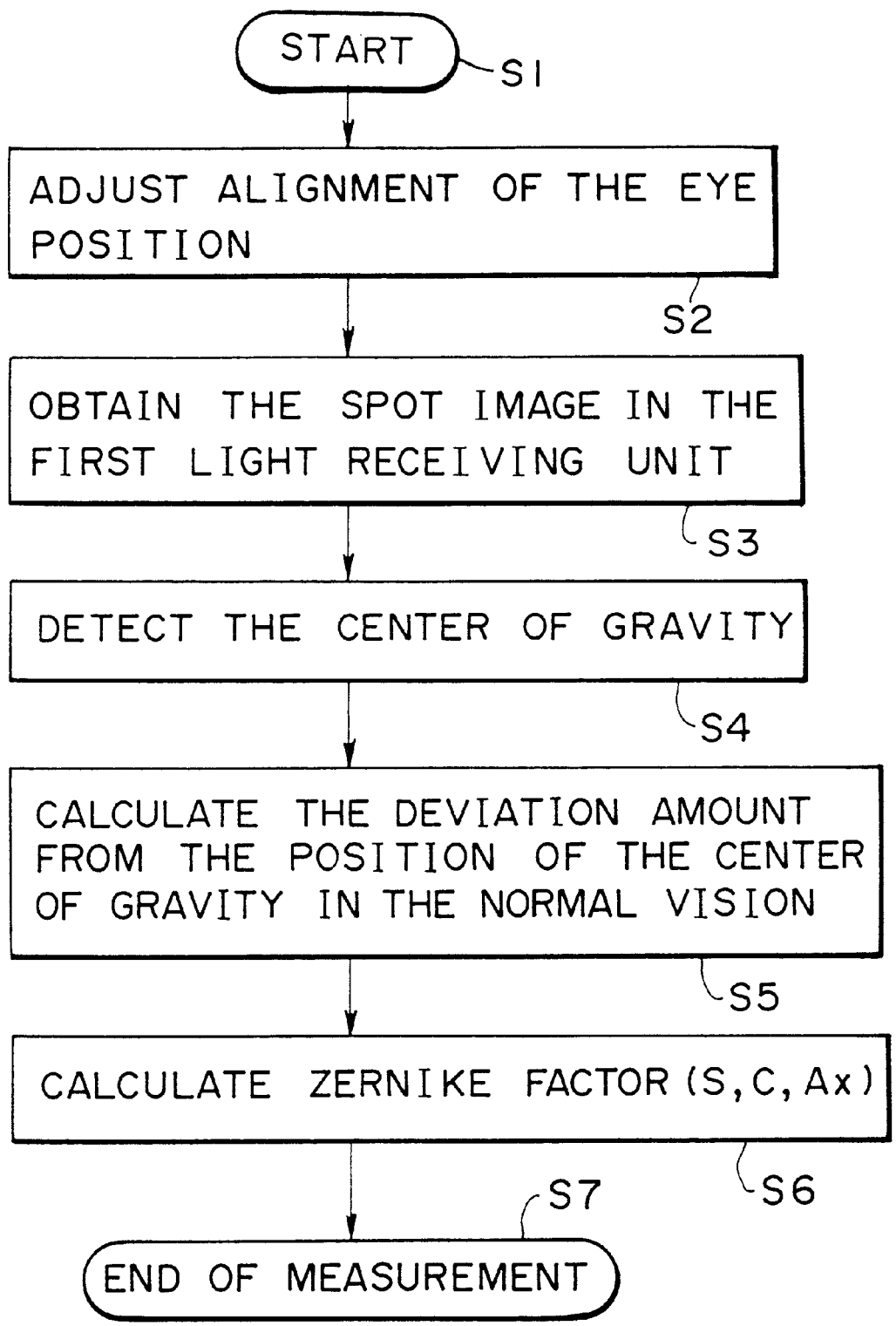

EYE CHARACTERISTIC MEASURING APPARATUS

BACKGROUND OF THE INVENTION

The present invention relates to an eye characteristic measuring apparatus where when optical characteristics of an eye are measured, a difference component from relation with measured data in a reference optical path is taken whereby measurement in high accuracy is performed, and particularly the measuring apparatus is provided with a reference optical system separate from a measurement light receiving system.

Measurement results of the eye characteristic measuring apparatus include both aberration of an eye and aberration of the measuring apparatus. Consequently in order to cancel aberration of equipment, measurement has been performed using an article to be measured without aberration previously.

In the above-identified conventional method, however, since data measured at the initial stage are used, a problem exists in that the measured aberration is included in strain of the equipment produced later or aberration of the equipment caused by deformation due to temperature.

Accordingly appearance of such an eye characteristic measuring apparatus has been desired strongly as aberration during the measurement can be removed completely and quite exact measurement can be performed.

SUMMARY OF THE INVENTION

The present invention consists in an eye characteristic measuring apparatus, where a reference optical system illuminates a small region on the opposite surface of the reference reflecting article by the luminous flux from the first light source, and receives the luminous flux reflected and returned from the reference reflecting article. The first conversion member divides the reflection luminous flux received in the measurement optical system and/or the reference optical system into a plurality of beams, the first light receiving unit receives the plurality of beams divided in the conversion member, and the changing unit guides the luminous flux in the measurement optical system and the reference optical system alternately to the first light receiving unit. The arithmetic control unit can estimate the optical characteristics of the eye based on the receiving position of the luminous flux from the measurement optical system obtained in the first light receiving unit and the receiving position of the luminous flux from the reference optical system. Therefore the present invention has quite excellent effects that the aberration during the measurement can be removed completely and quite exact measurement can be performed.

BRIEF DESCRIPTION OF THE DRAWINGS

The accompanying drawings show embodiments of the present invention, in which:

FIG. 4 is a flow chart explaining the operation of the first embodiment;

FIG. 5 is a flow chart explaining the operation of the first embodiment;

DESCRIPTION OF THE INVENTION

Embodiments of the present invention will be described referring to the accompanying drawings as follows.

First Embodiment

Figure 1:
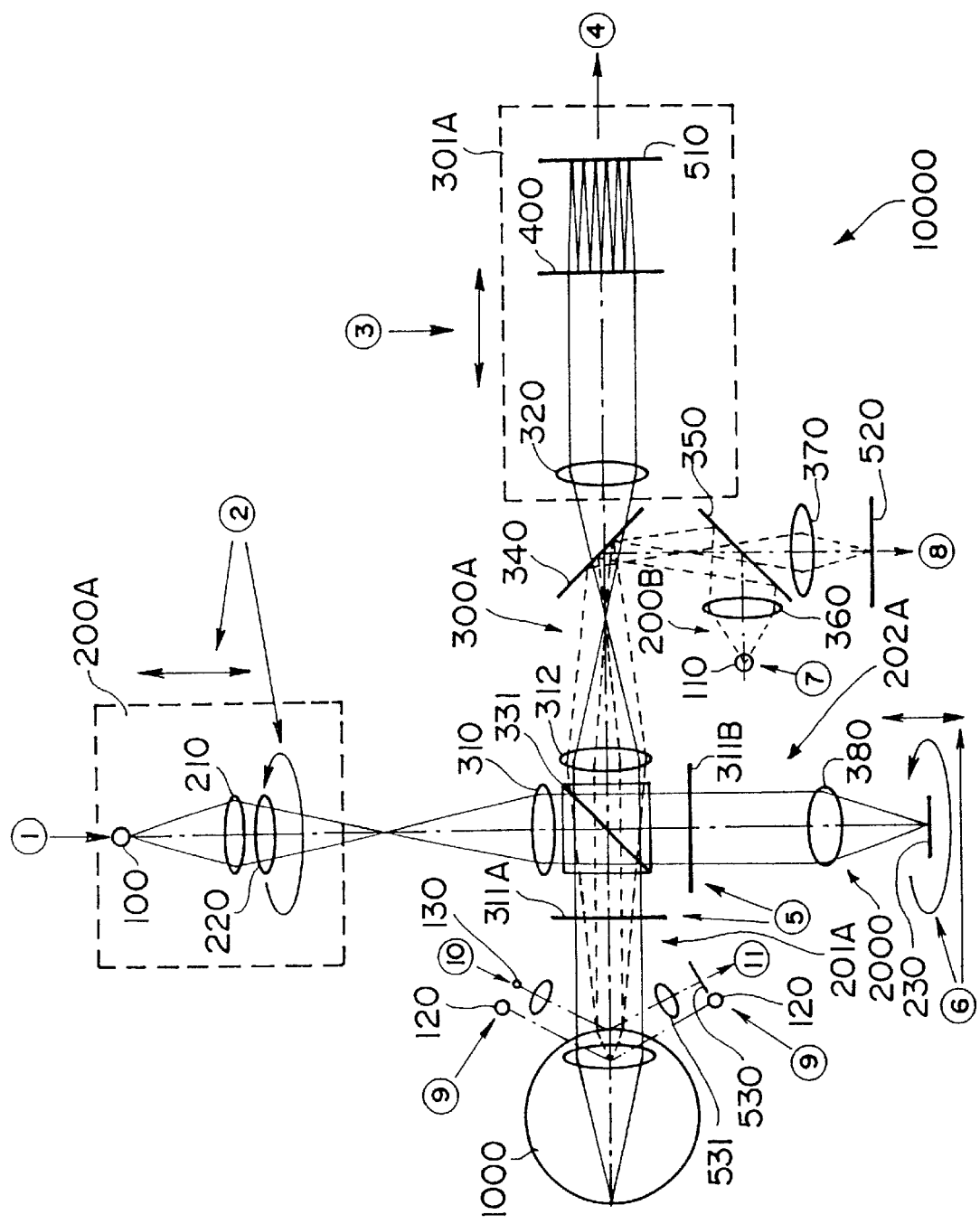
FIG. 1 is a diagram showing constitution of an eye characteristic measuring apparatus in a first embodiment.

An eye characteristic measuring apparatus 10000 in a fist embodiment according to the present invention, as shown in FIG. 1, includes a first light source 100 that emits luminous flux of a first wavelength, a first illuminating optical system 200A capable of illuminating a small region on the retina of the eye to be inspected with luminous flux from the first light source 100 in variable illuminating conditions, a first light receiving optical system 300A that guides a part of luminous flux reflected and returned from the retina of the eye to a first light receiving unit 510 through a first conversion member 400 that divides the reflected luminous flux into at least seventeen optical beams, a second illuminating optical system 200B where luminous flux from a second light source 110 passes through a condenser lens 360 and beam splitters 340, 350 and an eye 1000 being the object is illustrated by substantially parallel luminous flux, a second light receiving optical system 300B where the second optical flux reflected and returned from the front eye part is guided to a second light receiving unit 520 and an arithmetic unit 600 that determines the optical characteristics of the eye 1000 on the basis of a first signal provided by the first light receiving unit 510 corresponding to the inclination angle of the luminous flux. In addition, the first light source 100 corresponds to a first light source, and the first illuminating optical system 200A corresponds to a measurement optical system.

The arithmetic unit 600 controls all units and systems including a control unit 610. Further the control unit 610 receives signals ④,⑧,⑪ provided by the first light receiving unit 510, the second light receiving unit 520, a third light receiving unit 530, and controls the lighting and eliminating of the first light source 100 through the third light source 130, and drives a first driving unit 910 through a fourth driving unit 940 and controls a display unit 700 and a memory unit 800. In addition, the signal ④ from the first light receiving unit 510 can form setting data.

The first light source 100 preferably emits luminous flux being high in a spatial coherence and not high in a temporal coherence. In the first light source 100 in the first embodiment, an SLD is adopted and a point source with high luminance can be obtained.

Also the first light source 100 in the first embodiment is not limited to the SLD, but a light source with coherence being high in space and time, such as a laser, may be utilized in that a rotary diffusion plate or the like is inserted whereby the time coherence is reduced suitably.

Even a light source with coherence being not high in space and time, such as an SLD, can be used, if the quantity of light is sufficient, where a pinhole or the like is inserted in the position of the light source of the optical path.

A wavelength of the first light source 100 for illuminating in the first embodiment may be a wavelength in an infrared region, such as 780 nm.

The first illuminating optical system 200A illuminates a small region on the fundus of the eye to be inspected by luminous flux from the first light source 100. The first illuminating optical system 200A comprises the first light source 100, a first collimator lens 210 and a cylindrical lens 220, and illuminates the eye 1000 to be inspected.

The first light receiving optical system 300A receives luminous flux reflected and returned from a retina of the eye and guides the same to the first light receiving unit 510. The first light receiving optical system 300A comprises a first chopper 311A, a prism 331, a second afocal lens 312 and first light receiving means 301A. Also the first light receiving means 301A comprises a first collimate lens 320, a conversion member 400 for dividing the reflected luminous flux into at least seventeen beams and the first light receiving unit 510.

The beam splitter 331 is inserted in the first light receiving optical system 300A. The beam splitter 331 separates the light from the first illuminating optical system 200A, transmits one through a measuring optical system 201A toward the eye 1000 and transmits other through a reference optical path 202A toward a reference reflecting unit 2000.

Further the beam splitter 331 lets the scattering rays scattered in the eye 1000 to pass, reflects the scattering rays scattered in a reference reflection surface 2000A, and guides the reflected rays to the first light receiving optical system 300A. In FIG. 1, although the beam splitter 331 is constituted by a stuck prism having a beam splitter surface, the beam splitter 331 may be constituted by pellicle being a thin film. The beam splitter 331 is formed by a rhombus prism whereby an incident surface or an outgoing surface is slightly inclined from the perpendicular direction with respect to the optical axis. Thus influence of the bad reflected light can be reduced.

The reference optical path 202A is constituted by a second chopper 311B and a condenser lens 380. In the reference optical path 202A, a reference reflecting source 230 to be moved finely can be varied in its position in response to a spherical surface component of the eye to be inspected as the setting data.

Here the reference reflecting unit 2000 is constituted by a lens unit having at least refractive power, and a reflecting surface having a diffusion function. The reference reflecting unit 2000 is constituted, for example, by a model eye or the like. For aberration of the lens unit to be used in the model eye, aberration measured by design values and aberration measured by an interferometer in a certain determined diopter position are considered. In addition, the fundus of the model eye becomes a diffusion plate.

Figure 10:
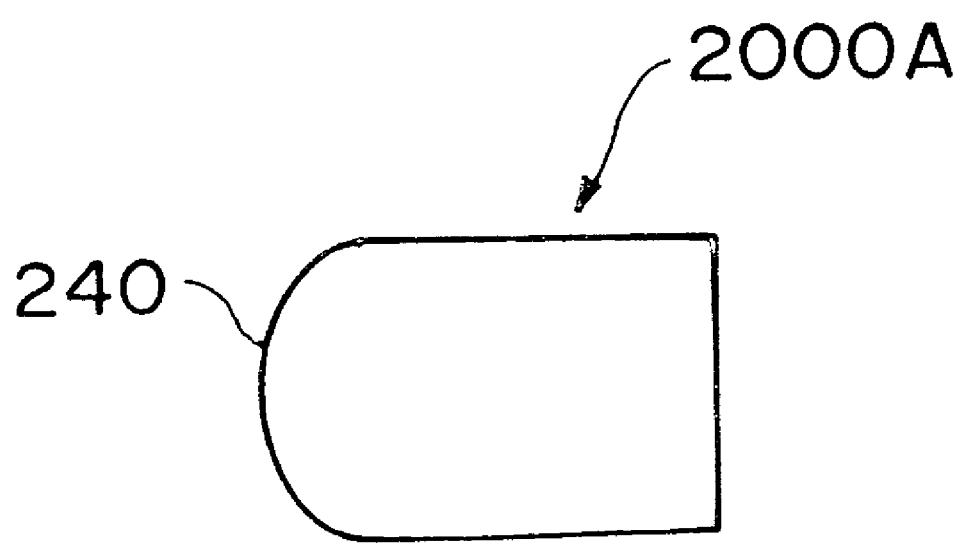
FIG. 10 is a diagram explaining a reference reflecting unit.

Also a reference reflecting unit as shown in FIG. 10, can be constituted by a glass rod 2000A comprising one surface formed by a spherical surface 240 and other surface formed by a diffusion plate 242. Here, the spherical surface 240 in one surface corresponds to a cornea, and the diffusion surface 242 corresponds to a retina. When a refractive power is measured, a plurality of glass rods 2000A being different in distance between the spherical surface 240 and the diffusion surface 242 in response to the spherical surface component are prepared, and suitable glass rods are selected and measured in response to the spherical surface component of the eye to be inspected. Otherwise the glass rods being different in the curvature radius and the distance between the curvature radius and, the spherical surface 240 and the diffusion surface 242 may be prepared and selected in response to the necessity.

When the cornea is measured, a plurality of glass rods 2000A being different in the curvature radius of the spherical surface 240 are prepared in response to the spherical component of the eye to be inspected, and suitable glass rods are selected and measured in response to the spherical surface component of the eye to be inspected.

Distance L between the reference reflecting unit 2000 and the fundus is adjusted corresponding to S of the eye 1000 to be inspected. That is, it follows that $L=f/(1+fD)$. Here, the focal distance of the lens unit is expressed as f and the refractive power of the eye 1000 to be inspected is expressed as D. In addition, the reference optical path 202A corresponds to the reference optical system.

If the first illumination optical system 200A is moved in the optical axis direction so that the point source is illuminated to the retina of the eye 1000 to be inspected, the degree of aberration of the luminous flux can be varied. In response to the variation, at least the reference reflecting unit 2000, and if necessary, the condenser lens 380, is moved in the optical axis direction so that the luminous flux of the first illumination optical system 200A is focused on the reference reflecting unit 2000 by the condenser lens 380 of the reference optical path 202A. The movement corresponds to the adjustment of so-called eye axis length.

The first light receiving unit 510 receives light from the first light receiving optical system 300A passing through the conversion member 400, and generates the first signal ④.

The fundus of the eye 1000 to be inspected and the reference reflecting surface 30 are conjugate with respect to the first light source 100, and the fundus of the eye 1000 to be inspected and the fundus of the reference reflecting surface 230 (corresponding to the fundus of the model eye) are conjugate with the first light receiving unit 510. Further the conversion member 400 is conjugate with the pupil, and the pupil is conjugate with a pupil of the reference reflecting surface 230.

That is, the front focus of the first afocal lens 310 is substantially coincident with the front part of the eye being the inspection object.

The first illumination optical system 200A and the first light receiving optical system 300A are deemed to be reflected in the point where the luminous flux from the first light source 100 is converged. While relation for the signal peak in the first light receiving unit 510 to become maximum by the reflected light is maintained, the first illumination optical system 200A and the first light receiving optical system 300A are moved in conjucation in the direction of strengthening the signal peak in the first light receiving unit 510 and are stopped at the position where the intensity becomes maximum. As a result, the luminous flux from the first light source 100 is converged on the fundus of the eye. It is preferable that the first light source 100 is lit for a definite short time after the necessary preparation is made.

Next, the transforming member 400 will be described.

The transforming member 400 arranged in the first light receiving optical system 300A is a wavefront transforming unit that converts the reflected luminous flux into a plurality of optical systems, the transforming member 400 employed in the first embodiment comprises a plurality of micro Fresnel lenses arranged in a plane perpendicular to the optical axis.

Figure 9B:
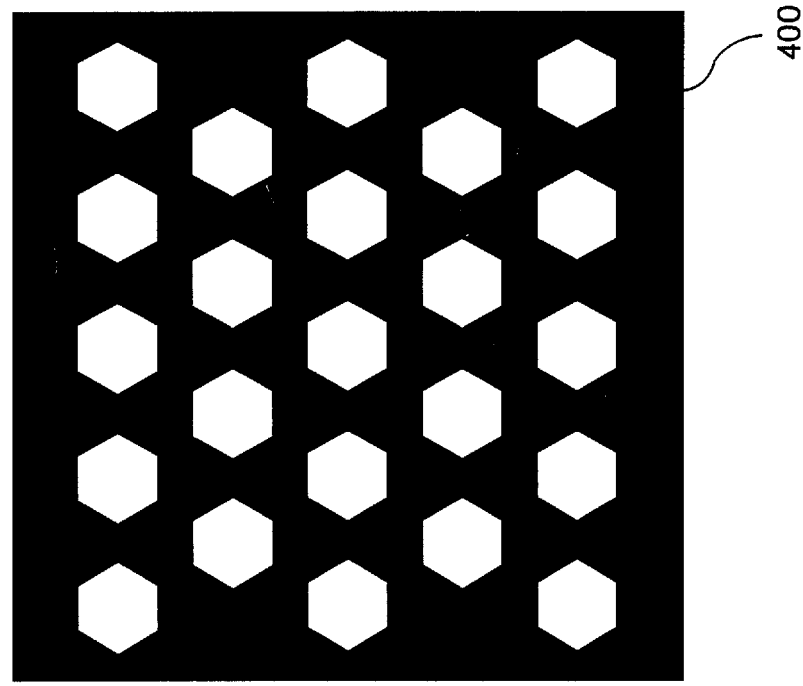
FIGS. 9(a) (b) are diagrams explaining apertures of Hartman's plate.
Figure 9A:
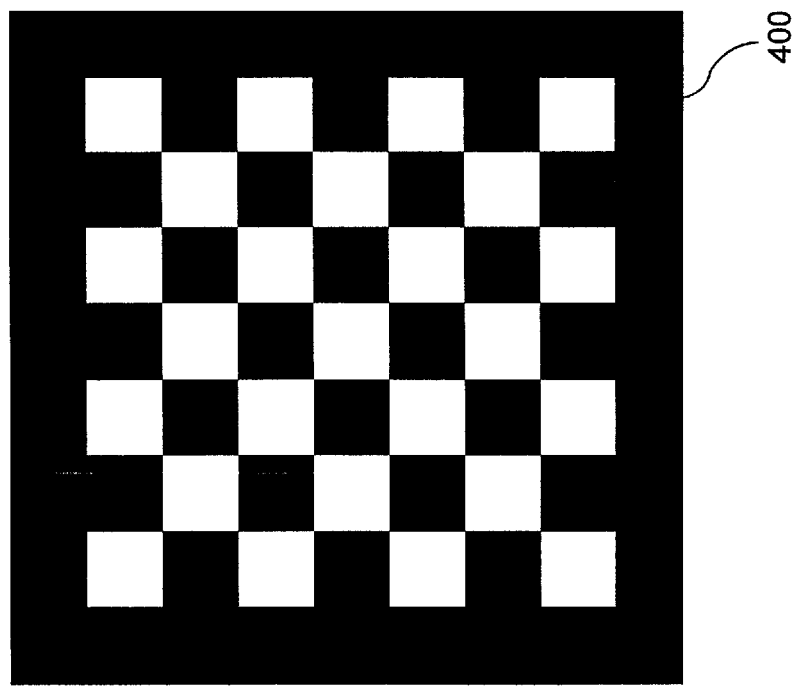

In order to measure the measurement object in the spherical component and the astigmatism in the third order, the measurement must be performed at least using 17 beams through the measurement object. An example of the transforming member will be shown in FIG. 9(*a*) and FIG. 9(*b*). In any case, the center aperture is arranged in conformity with the optical axis of the optical system.

Here, the micro Fresnel lens will be described in detail.

The micro Fresnal lens is an optical element having annular ridges arranged at a height pitch for a wavelength and having a blaze angle optimum for an outgoing light in parallel to the converging point. The micro Fresnel lens capable of being utilized here is, for example, that having the difference of the optical path length of eight levels applying the semiconductor precise machining technology effectively, and the converging efficiency of 98% can be realized.

The reflected light from the fundus of the eye passes through the second afocal lens 312, the collimator lens 320 and the transforming unit 420 and is focused as first order light on the first light receiving unit 510. Here zero-order light corresponds to transmitted luminous flux and the first-order light corresponds to condensed light.

The transforming member 400 may comprise a micro lens unit for performing converging function and an opening unit for performing transmitting function, in each of regions divided in at least seventeen regions.

The transforming member 400 in the first embodiment comprises a wave front transforming member for converting the reflected luminous flux into at least seventeen beams, Next the first light receiving unit 510 receives the plurality of optical beams converted in the transforming member 400. In the first embodiment, the first light receiving unit 510 is CCD that does not generate much read-out noise, the CCD may be of any type of general CCD with low-noise or a cooled CCD for measurement provided with 2000*2000 elements.

An image signal output from a low-noise CCD and its driver can be simply achieved by using an adaptive image input board.

The first light receiving optical system 300A has a substantially conjugate-relation with an iris of an eye and the transforming member 400.

A prism 331 is inserted in the first light receiving optical system 300A, and light from the first illuminating optical system 200A is sent to the eye 1000 and the reflected light is transmitted.

Further a working distance adjusting optical system for adjusting a working distance between the eye 1000 being the object and an optical characteristic measuring apparatus 10000, an alignment optical system for adjusting the positional relation of the eye 1000 being the object and the optical characteristic measuring apparatus 10000 in the direction perpendicular to the optical axis, and a second illuminating optical system 200B for illuminating the object are provided.

The alignment is performed as follows. Luminous flux from the second light source 110 of the second illuminating optical system 200B passes through a light converging lens 360, the beam splitter 350 and the beam splitter 340, and the eye 1000 being the object is illuminated by luminous flux being substantially in parallel. The reflection luminous flux reflected in the cornea of the eye is emitted in the divergent luminous flux as if it was emitted from the point of ½ of the cornea curvature radius. The divergent luminous flux passes through the beam splitter 350 being the second light receiving optical system 300B, the beam splitter 340 and a light converging lens 370, and is received as a spot image in the second light receiving unit 520. When the spot image is deviated from the optical axis on the second light receiving unit 520, the main body of the characteristic measuring apparatus 10000 is moved and adjusted in the vertical direction and the lateral direction so that the spot image comes on the optical axis. When the spot image is coincident with the optical axis on the second light receiving unit 520, the alignment adjustment is completed.

The wavelength of the second light source 110 is different from the wavelength of the first light source 100, and the wavelength larger than this, for example, 940 nm can be selected. In addition, the second light source 110 and the pupil of the eye are conjugate with each other, and the pupil of the eye and the second light receiving unit 520 are conjugate with each other.

The beam splitter 340 is formed in a dichroic mirror so that the wavelength of the first light source 100 is transmitted and the wavelength of the second light source 110 is reflected, and thereby such state is prevented that the luminous flux in one optical system enters another optical system and noise is produced.

Next, the working distance adjustment is performed in that the luminous flux emitted from the fourth light source 130 is irradiated toward the object, and light reflected from the eye being the object is received through the converging lens 531 by the third light receiving unit 530. The third light receiving unit 530 suffices if it can detect variation of the luminous flux position within the surface including the fourth light source 130, the optical axis and the third light receiving unit 530. For example, it can be constituted by the one-dimensional CCD and the position sensing device (PSD) arranged within the surface.

When the eye is at the proper working distance, the spot image from the fourth light source 130 is formed on the optical axis of the third light receiving unit 530, and when the eye is deviated from the proper working distance forward or rearward, the spot image is formed upward or downward from the optical axis.

Figure 2:
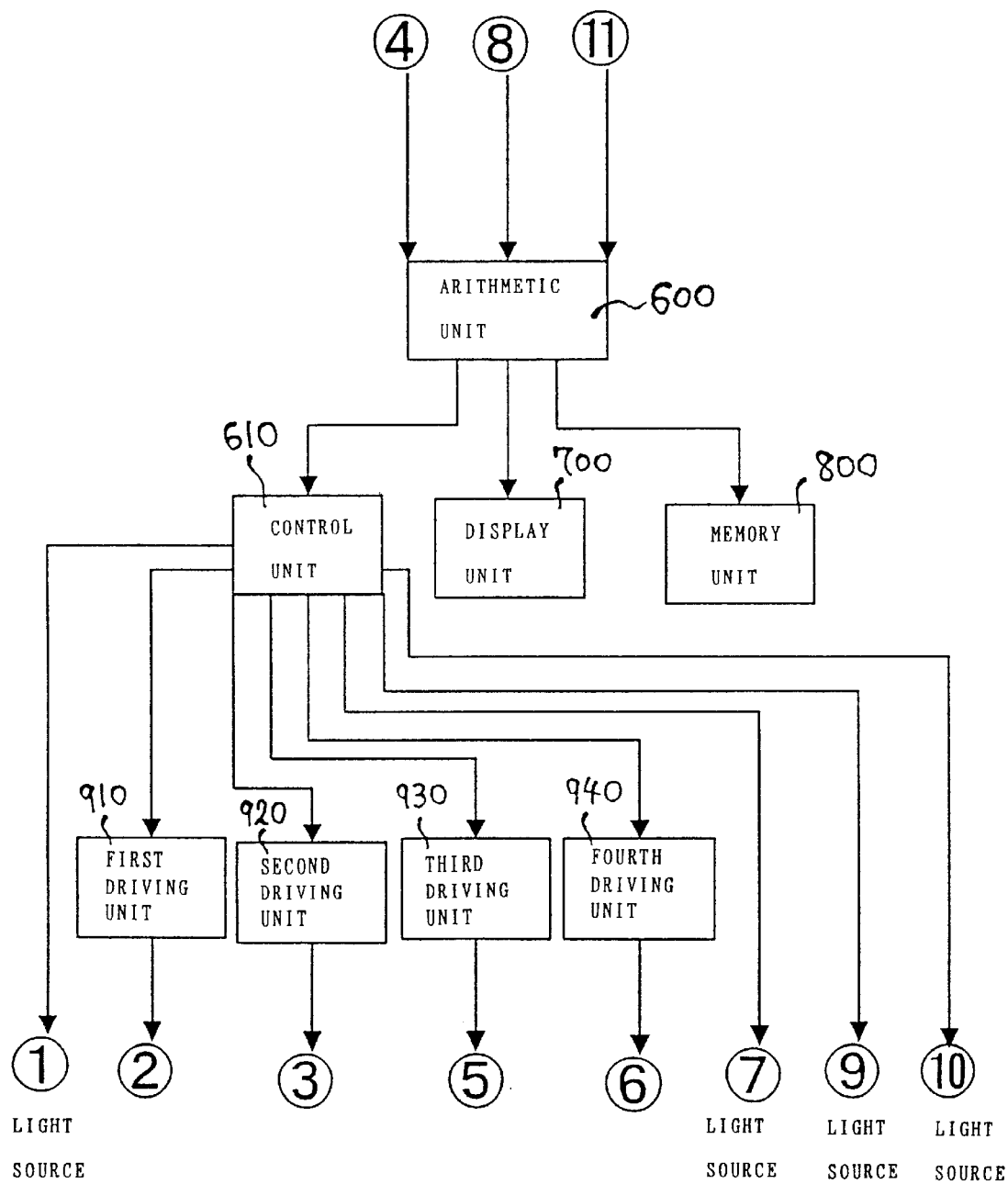
FIG. 2 is a diagram showing electric constitution of the eye characteristic measuring apparatus in the first embodiment.

Here the electric constitution of the eye characteristic measuring apparatus 10000 will be described. based on FIG. 2. The electric constitution of the eye characteristic measuring apparatus 10000 comprises an arithmetic unit 600, a control unit 610, a display unit 700, a memory unit 800, a first driving unit 910, a second driving unit 920, a third driving unit 930 and a fourth driving unit 940.

The control unit 610 controls lighting and eliminating of the first light source 100 through the fourth light source 130, and also controls the first driving unit 910, the second driving unit 920, the third driving unit 930 and the fourth driving unit 940 in response to a signal provided by the arithmetic circuit 600.

The first driving unit 910 moves the first illuminating optical system 200A as a whole in the optical axis direction, based on a signal from the first light receiving unit 510 inputted to the arithmetic unit 600, or rotates and adjusts the first cylinder lens 220 of the first illuminating system 200A around the optical axis. The first driving unit 910 drives suitable lens moving means so that the illuminating optical system 200A is moved and adjusted. Consequently the first driving unit 910 moves the first illuminating optical system 200A in the optical axis direction so that a point source is illuminated to a retina of the eye to be inspected.

The second driving unit 920 drives the first light receiving optical system 300A as a whole in the optical axis direction, based on a signal from the first light source receiving unit 510 inputted to the arithmetic unit 600. The second driving unit 920 drives suitable lens moving means so that the first light receiving optical system 301A is moved and adjusted.

The third driving unit 930 controls, drives the first chopper 311A and the second chopper 311B, based on a control signal from the arithmetic unit 600.

The first chopper 311A and the second chopper 311B disposed at the outgoing side of the prism 331 correspond to a changing unit and an analyzer, and can change light from the first illuminating optical system 200A alternately to the measurement optical system 201A and the reference optical path 202A.

If the arithmetic unit 600 drives the third driving unit 930, opens the first chopper 311A being at the side of the eye 1000 to be inspected and closes the second chopper 311B being at the side of the model eye, the measurement optical system 201A is selected. On the contrary, if the first chopper 311A being at the side of the eye 1000 to be inspected is closed and the second chopper 311B being at the side of the model eye is opened, the reference optical path 202A is selected.

In addition, the prism 331 performs separation into the measurement optical system 201A which reflects the light from the first illuminating optical system 200A and directs the same toward the eye 1000 to be inputted, and the reference optical path 202A which makes the light from the first illuminating optical system 200A transmit and directs the same toward the reference reflecting unit 2000. A polarization beam splitter may be used as the prism 331. For example, a polarization beam splitter performing reflection in the S polarization and performing transmission in the P polarization may be adopted, and an analyzer performing transmission in the S polarization or the P polarization may be arranged within the first light receiving optical system 300A.

The reference optical path 202A is constituted by the second chopper 311B and the condenser lens 380. The reference reflecting unit 200 capable of being moved finely is arranged in the reference optical path 202A. In addition, the reference reflecting unit 2000 corresponds to a reference reflecting article.

The fourth driving unit 940 moves the reference reflecting unit 2000 finely, based on a control signal from the arithmetic unit 600. The reference reflecting unit 2000 is constituted by a suitable diffusion plate. The reference reflecting unit 2000 is moved finely whereby influence of noise in a speckle or the like can be removed. The reference reflecting unit 2000 of revolver type may be used where several sorts can be changed.

Figure 3A:
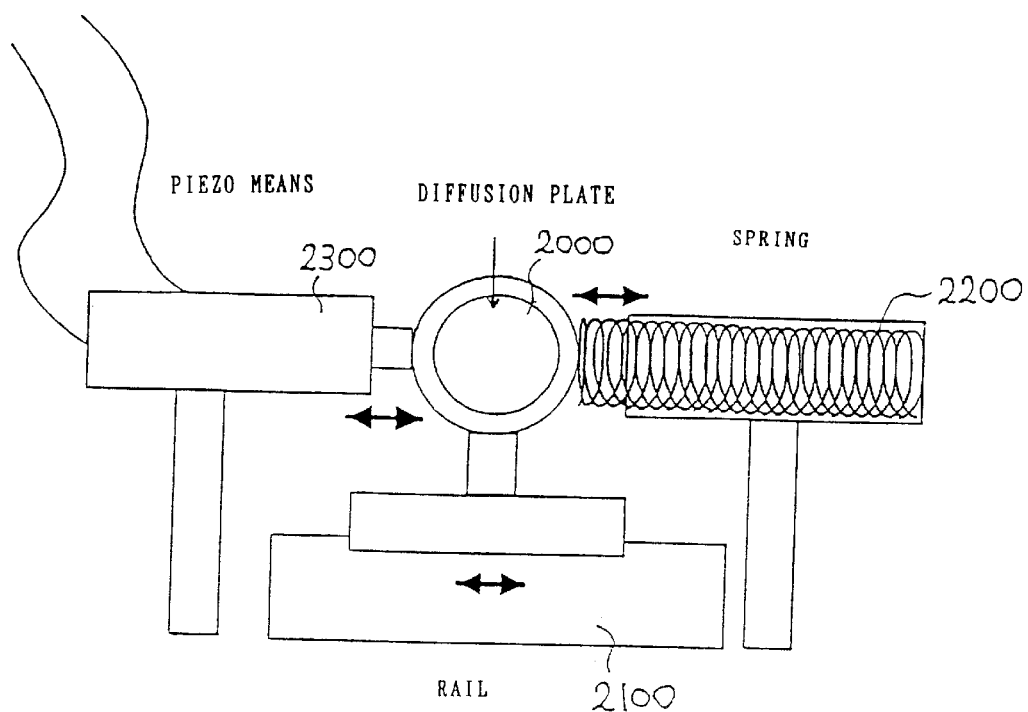
FIG. 3(a) is a diagram explaining an example of a fourth driving unit.

In the fourth driving unit 940, for example, as shown in FIG. 3(a), the reference reflecting unit 2000 is arranged on a rail 2100 movable in the lateral direction, and the reference reflecting unit 2000 is stood against elastic restoring force of the spring 2200 and the piezo means 2300 is driven whereby the reference reflecting unit 2000 can be moved.

Figure 3B:
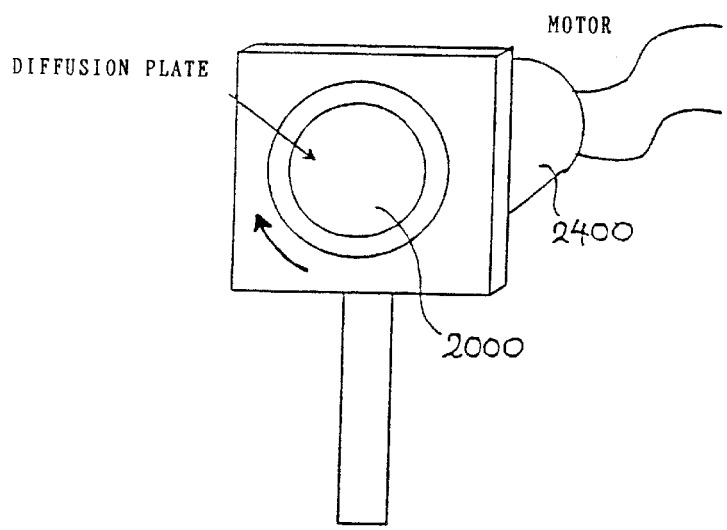
FIG. 3(b) is a diagram explaining an example of the fourth driving unit.

Also the fourth driving unit 940, as shown in FIG. 3(b), may be constituted in that a motor 2400 is coupled with the reference reflecting unit 2000, and the reference reflecting unit 2000 is rotated.

Figure 3C:
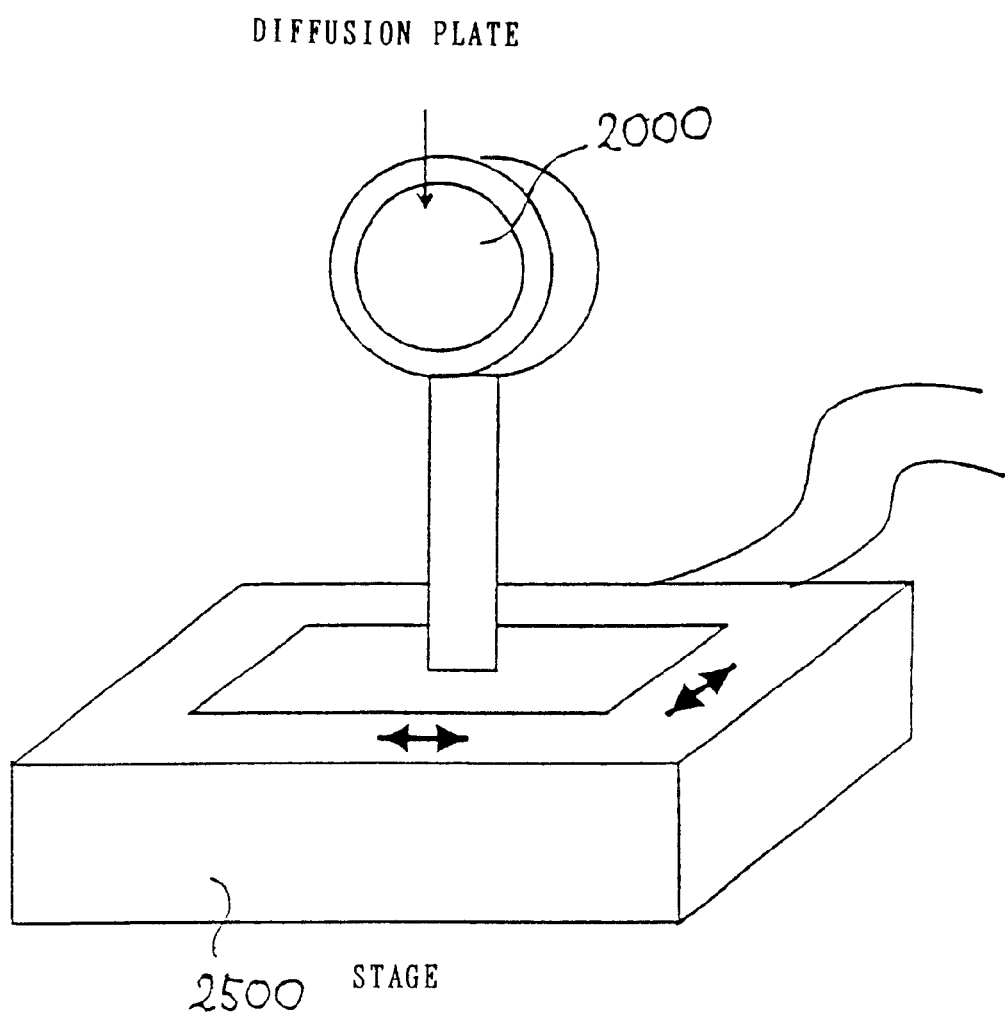
FIG. 3(c) is a diagram explaining an example of the fourth driving unit.

Further the fourth driving unit 940, as shown in FIG. 3(c), may be constituted in that the reference reflecting unit 2000 is mounted on a stage 2500 which can be moved in the two-dimensional direction, and the reference reflecting unit 2000 can be moved finely.

At first, measurement of the whole system will be explained based on FIG. 6.

At first, the measurement is started at step S1. Next, in step S2, in order to measure the setting data, the arithmetic unit 600 drives the third driving unit 930, and the first chopper 311 being at the side of the eye 1000 to be inspected is opened, and the second chopper 311B being at the side of the model eye is closed.

At step S3, "the measurement of the eye (A-2)" in FIG. 5 as explained later in detail is performed, the measurement results of the eye including aberration existing in the first light receiving optical system are measured, and the setting data so as to set the reference reflecting unit 2000 together with the eye are estimated. The setting data are obtained concretely in that the spot image at the normal vision is obtained temporarily, and the deviation amount from the position of the center of gravity in the spot image in the normal vision is obtained from the eye to be inspected and the setting data are obtained in the position of the center of gravity (S, C, Ax).

At step S4, the arithmetic unit 600 drives the third driving unit 930 based on the setting data estimated in step S3, and the second chopper 311B being at the side of the model eye is opened, and the first chopper 311A being at the side of the eye 1000 to be inspected is closed.

At step S5, "the measurement of the reference reflecting unit (A-1)" is executed. That is, in the reference reflecting unit, in response to the refractive power of the eye to be inspected, distance between the condenser lens unit 380 and the reference reflecting surface 230 is adjusted. Concretely in response to the refractive power of the eye and the curvature of the cornea, it follows that the distance becomes $L=f/(1+fD)$. Here the focal length is expressed as f, and the refractive power of the eye 1000 is expressed as D.

Further in step S6, the deviation amount of the position of the center of gravity of the spot image on the first light receiving unit 510 between the eye 1000 to be inspected and the reference reflecting unit 2000 (model eye) is calculated.

In step S7, based on the expression 4 and the expression 5 as described later, Zernike factor is calculated.

In step S8, calculated S, C, Ax, SA, Coma and such are displayed on the display unit 700.

In step S9, decision is performed regarding whether the measurement is finished or not. When the measurement is finished, process is advanced to step S10 and then terminated. Also when the measurement is not finished in step S10, process is returned to step S2.

Among the flow chart as above described, process of "the measurement of the eye (A-2)" executed in step S3 will be explained based on FIG. 5 as follows.

Measurement of the Eye (A-2)

In step 1 (hereinafter abbreviated as "S1"), the measurement is started. Next, in step S2, the alignment of the position of the eye to be inspected is adjusted.

In step S3, the spot image is picked up by the first light receiving unit 510. Next, in step S4, The position of the center of gravity is detected.

Further in step S5, the deviation amount from the position of the center of gravity in the normal vision is calculated. Here, the position of the center of gravity in the normal vision means the position of the center of gravity of the condensed luminous flux formed on the first light receiving unit 510 by the conversion member 400 from the luminous flux reflected from the fundus of the eye to be inspected, when the eye in the normal vision is measured.

In step S6, based on the expression 4 and the expression 5 as described later, Zernike factor is calculated. After the Zernike factor is calculated in step S6, process is advanced to step S7, and the measuring is finished.

Among the flow chart as above described, process of "the measurement of the reference reflecting unit (A-1)" performed in step S5 will be described based on FIG. 4 as follows.

Measurement of the Reference Reflecting Unit (A-1)

The measurement of the reference reflecting unit will be explained based on FIG. 4. In step S1 (hereinafter abbreviated as "S1"), the measurement is started. Next, in step S2, the reference reflecting unit 2000 (model eye) near S, C, Ax of the eye 1000 is set. In step S3, the image data are obtained from the first light receiving unit 510.

Further in step S4, the position of the center of gravity may be estimated. For example, luminous flux is projected on a plurality of picture elements in the light receiving surface, and the intensity of the luminous flux of each picture element is referred to so that the position of the center of gravity is estimated. The position of the center of gravity is calculated in such manner to secure the accuracy of the measurement position being $\frac{1}{10}$ of the element or less. After the position of the center of gravity is detected in step S5, the measurement of the reference reflecting unit 2000 is finished in step S5.

Second Embodiment

An eye characteristic measuring apparatus 20000 in a second embodiment of the present invention has optical constitution to measure the cornea shape. Optical constitution shown in FIG. 7 is substantially similar to that in the first embodiment and a cornea can be measured.

Figure 7:
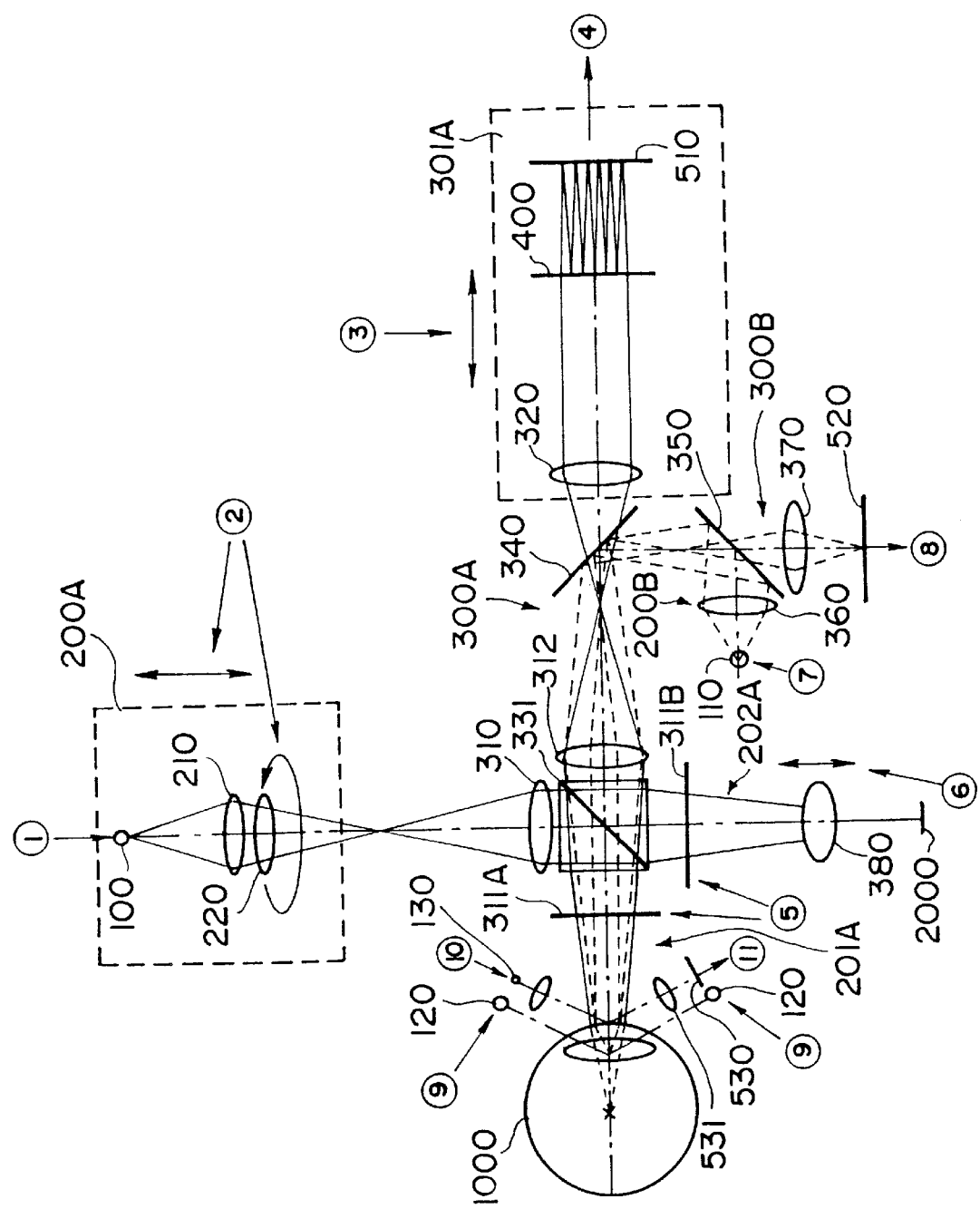
FIG. 7 is a diagram explaining optical constitution of an optical characteristic measuring apparatus in a second embodiment.

Referring to FIG. 7, the second embodiment will be described mainly regarding the point different from the first embodiment. In a light receiving optical system, a first light receiving unit 510 is arranged in conjugate relation with the curvature center of a cornea of an eye to be inspected through an objective lens 310 and a collimator lens 320, in the state that suitable working distance is adjusted by output of a third light receiving unit 530 being a working distance optical system and suitable alignment is adjusted by output of a second light receiving unit 520 being an alignment optical system. That is, a first light source 100 is conjugate with the curvature center of a cornea of the eye 1000 and the curvature center of a reference reflecting unit 2000 (model eye) is conjugate with the first light receiving unit 510. Further the second light source 110 is conjugate with a pupil of the eye 1000 to be inspected, and the pupil is conjugate with the second light receiving unit 520.

Alignment is performed as follows. Luminous flux from the second light source 110 of the second illuminating optical system 200B passes through a condenser lens 370 and beam splitters 350, 340 and the eye 1000 being an object is illuminated by substantially parallel luminous flux. Luminous flux reflected in the cornea of the eye to be inspected is emitted as if it were divergent bundle of rays emitted from the point of ½ of the curvature radius of the cornea. The divergent bundle of rays pass through the beam splitters 350, 340 and the condenser lens 370 being the second light receiving optical system 300B and are received as a spot image in the second light receiving unit 520. When the spot image is out of the optical axis on the second light receiving unit 520, the body of the optical characteristic measuring apparatus 10000 is moved and adjusted in vertical direction and lateral direction so that the spot image comes onto the optical axis.

A wavelength of the second light source 110 is different from that of the first light source 100, and a wavelength longer than this, for example, 940 nm can be selected.

The position of the front focus of a second afocal lens 312 is different from that of the first embodiment and is substantially coincident with that of the cornea of the eye.

In the state that the suitable working distance and the suitable alignment are adjusted, the first illuminating optical system 200A is moved and adjusted so that the illuminating luminous flux of the first illuminating optical system 200A is converged toward curvature center of the cornea of the eye 10000 to be inspected.

Regarding whether the illuminating luminous flux of the first illuminating optical system 200A is converged toward the curvature center of the cornea of the eye 10000 correctly or not, the first illuminating optical system 200A is finely moved in the optical axis direction so that the output of the first light receiving unit 510 becomes maximum at the front side and the rear side of the position of the first illuminating optical system.

Regarding the cornea shape, first, in the state that adjustment of the suitable working distance is performed, the first illuminating optical system 200A and the first light receiving optical system 300A in association with this are moved so that the luminous flux from the first illuminating optical system 200A is converged to the curvature center of the cornea. When the output of the first light receiving optical system 300A becomes maximum, the distance between the apex position of the cornea and the converging position of the first light receiving optical system 300A corresponds to the curvature radius of the cornea.

That is, the adjustment of the working distance has been completed.

If the first illuminating optical system 200A is moved in the optical axis direction so that the luminous flux is converged to the curvature center of the cornea of the eye 1000 to be inspected, the degree of aberration of the luminous flux can be varied. In response to the variation, the lens 380 is moved in the optical axis direction so that the luminous flux of the first illuminating optical system 200A is converged toward the curvature center at the front side of the lens 380. This corresponds to the adjustment of the so-called eye axial length.

Figure 6:
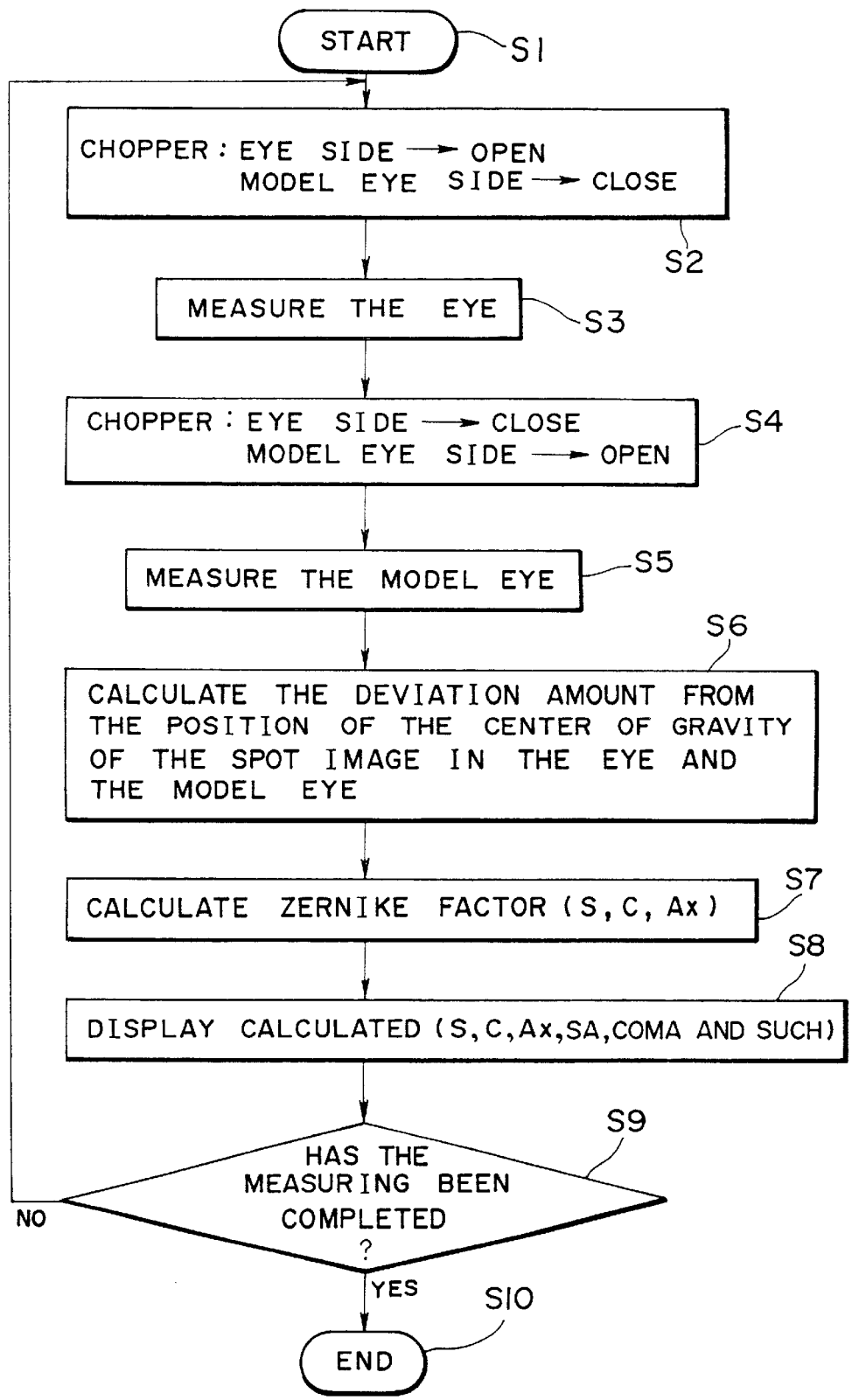
FIG. 6 is a diagram explaining the operation of the first embodiment.

Concrete measuring method and procedure in the second embodiment are similar to that of FIG. 6 described in the first embodiment. Therefore the detailed description shall be omitted.

The Zernike polynominal estimated in the process represents optical characteristics (shape, curvature radius, power and the like) of the cornea.

In addition, other constitution, function and the like are similar to that in the first embodiment. Therefore the detailed description will be omitted.

Third Embodiment

The optical characteristic measuring apparatus 10000 for measuring refractive power in the first embodiment and the optical characteristic measuring apparatus 20000 for measuring the cornea shape in the second embodiment may be used in combination.

The principle of operation of the arithmetic unit 600 for determining the optical characteristics of the eye 1000 on the basis of the first signal provided by the first photodetecting device 510 and corresponding to the inclination of light will be explained.

The present invention is intended to measure the wave aberration of the eye.

The coordinate system XY is defined by an x-axis and a Y-axis on the transforming device 400 and a coordinate system xy is defined by an x-axis and a y-axis on the first photodetecting device 510. A wavefront W(X,Y) expressed by Expression (3) is determined by Expressions (1) and (2).

$$\frac{\partial W(X,Y)}{\partial X} = \frac{\Delta x}{f} \quad \text{Expression (1)}$$

$$\frac{\partial W(X,Y)}{\partial Y} = \frac{\Delta y}{f} \quad \text{Expression (2)}$$

$$W(X,Y) = \sum_{i=0}^{n} \sum_{j=0}^{i} c_{ij} Z_{ij}(X,Y) \quad \text{Expression (3)}$$

Both sides of Expression (3) are differentiated by X and Y to obtain derivatives, and the derivatives are substituted into the left sides of Expressions (1) and (2) to obtain a polynomial of $C_{ij}$.

$Z_{ij}$ of Expression (3) is called Zernike polynomial expressed by Expressions (4) and (5).

$$Z_{nm} = R_n^{n-2m}(r) \left\{ \genfrac{}{}{0pt}{}{\sin}{\cos} \right\} (n-2m)\theta$$

where when n−2m>0, sin is applied and when n−2m≦0, cos is applied.

$$R_n^{n-2m}(r) = \sum_{S=0}^{m} (-1)^S \frac{(n-S)!}{S!(m-S)!(n-m-S)!} r^{n-2S} \quad \text{Expression (5)}$$

Unknowns $C_{ij}$ are determined by reducing the mean square error of Expression (6) to a minimum.

$$S(x) = \sum_{i=i}^{data\ number} \left[ \left\{ \frac{\partial W(X_i, Y_i)}{\partial X} - \frac{\Delta x_i}{f} \right\}^2 + \left\{ \frac{\partial W(X_i, Y_i)}{\partial Y} - \frac{\Delta y_i}{f} \right\}^2 \right] \quad \text{Expression (6)}$$

The $C_{ij}$ thus determined are important optical parameters of the eye.

In Zernike polynomial, symbols indicate the followings.
$Z_{10}, Z_{11}$: Prisms
$Z_{21}$: S
$Z_{20}, Z_{22}$: C, Ax
$Z_{30}, Z_{33}$: Arrow aberration
$Z_{31}, Z_{32}$: Third-order coma aberration
$Z_{42}$: Third-order spherical aberration
$Z_{41}, Z_{43}$: Astigmatism
$Z_{52}, Z_{53}$: Fifth-order coma aberration
$Z_{63}$: Fifth-order spherical aberration
$Z_{84}$: Seventh-order spherical aberration Regarding Removing of Aberration of Equipment by Reference Reflecting Unit 2000

X-Y plane (pupil) and X1-Y1 plane (Hartman's plate) are conjugate optically to each other (magnification:β). f is distance between the Hartman's plate (400) and the CCD (first light receiving unit 510) and is equal to the focal length of the microlens of the Hartman's plate (400).

Figure 8:
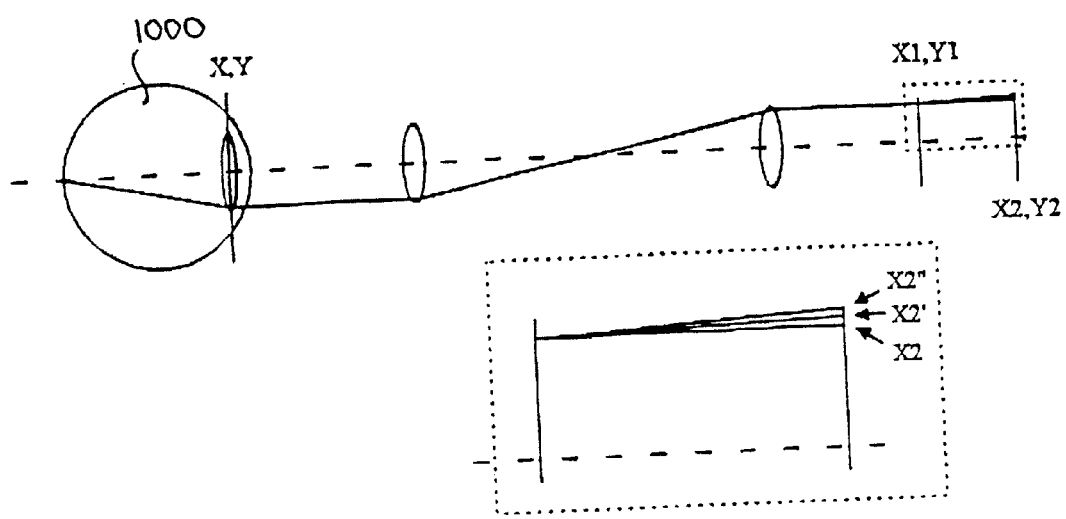
FIG. 8 is a diagram explaining the principle.

As shown in FIG. 8, if X2 is expressed as the position of the point of the Hartman's image when the optical system of the measuring instrument has no aberration, X2' is expressed as the position of the point of the Hartman's image including only aberration of the measuring instrument, and X2" is expressed as the position of the point of the Hartman's image including aberration of the eye 1000+aberration of the measuring instrument, the wavefront aberration WT including the aberration of the eye 1000 and the aberration of the measurement optical system of the measuring instrument is expressed by following Expression.

$$\left. \begin{array}{l} \frac{\partial W_T}{\partial X} = \frac{X2'' - X2}{f} \\ \frac{\partial W_T}{\partial Y} = \frac{Y2'' - Y2}{f} \end{array} \right\} \quad \text{Expression (7)}$$

Expression regarding Y is obtained by changing X to Y. Therefore Expression regarding Y will be omitted.

Here, if $W_R$ is expressed as wavefront aberration of the measurement optical system of the measurement optical system of the measuring instrument, it follows that $$\frac{\partial W_R}{\partial X} = \frac{X2' - X2}{f} \quad \text{Expression (8)}$$

where if $W_E$ is expressed as wavefront aberration of the eye to be measured, it follows that $$\frac{\partial W_E}{\partial X} = \frac{X2'' - X2'}{f} \quad \text{Expression (9)}$$

X2 seems also the reference point in the calculation, and in the calculation with this point being the reference point, the wavefront aberration $W_T$ includes the aberration of the eye and the aberration of the measuring apparatus. Consequently in order to cancel the aberration of the equipment, in the prior art, the aberration of the equipment has been performed in advance using an article without aberration.

In this method, however, since data measurement at the initial stage are used, the measured aberration is included in strain of the equipment produced later or aberration of the equipment caused by deformation due to temperature. Consequently $W_T$ is equal to the aberration of the reference reflecting unit 2000+the aberration produced after the initial measurement.

In the present invention, the reference optical path is measured at every time, and the position of the spot measured then is expressed as X2' whereby the aberration during the measurement can be removed completely and quite exact measurement can be performed.

That is, utilizing Expression (8), $$\frac{\partial (W_T - W_R)}{\partial X} = \frac{X2'' - X2'}{f} \quad \text{Expression (10)}$$

can be obtained.

In the present invention constituted as above described, the first light source emits luminous flux of a first wavelength, and the measurement optical system illuminates an object surface of an eye to be inspected by luminous flux from the first light source, receives luminous flux reflected and returned from the object surface of the eye. The reference optical system illuminates a small region on the opposite surface of the reference reflecting article by the luminous flux from the first light source, and receives the luminous flux reflected and returned from the reference reflecting article. The first conversion member divides the reflection luminous flux received in the measurement optical system and/or the reference optical system into a plurality of beams, the first light receiving unit receives the plurality of beams divided in the conversion member, and the changing unit guides the luminous flux in the measurement optical system and the reference optical system alternately to the first light receiving unit. The arithmetic control unit can estimate the optical characteristics of the eye based on the receiving position of the luminous flux from the measurement optical system obtained in the first light receiving unit and the receiving position of the luminous flux from the reference optical system. Therefore the present invention has quite excellent effects that the aberration during the measurement can be removed completely and quite exact measurement can be performed.

What is claimed is:

1. An eye characteristic measuring apparatus comprising:
   a light source for emitting luminous flux of a wavelength;
   a measurement optical system for illuminating an object surface of an eye to be inspected by luminous flux from said light source, and for receiving the luminous flux reflected and returned from the object surface of the eye;
   a reference optical system for illuminating a small region on a reflecting surface of a reference reflecting article by luminous flux from said light source, and for receiving the luminous flux reflected and returned from the reference reflecting article;
   a conversion member for dividing reflection luminous flux into a plurality of optical beams, said reflection luminous flux being received in said measurement optical system and/or said reference optical system;
   a light receiving unit for receiving the plurality of optical beams converted by said conversion means;
   a changing means for guiding optical beams of said measurement optical system and said reference optical system alternately to said light receiving unit; and
   an arithmetic control unit for estimating optical characteristics of the eye to be inspected, based on a receiving position of luminous flux from said measurement optical system obtained in said light receiving unit and a receiving position of luminous flux from said reference optical system.

2. An eye characteristic measuring apparatus as set forth in claim 1, wherein the arithmetic control unit estimates setting data from an output signal of the light receiving unit when luminous flux from the measurement optical system is received, and based on the thus estimated setting data, condition of the reference reflecting article of the reference optical system is set.

3. An eye characteristic measuring apparatus as set forth in claim 2, wherein the object surface of the eye to be inspected is a retina of the eye, said measurement optical system is constituted so that a small region of a retina of the eye to be inspected is illuminated with the luminous flux, and the arithmetic control unit estimates optical characteristics of refractive power of the eye.

4. An eye characteristic measuring apparatus as set forth in claim 2, wherein the object surface of the eye is a cornea of the eye, and the measurement optical system is adapted to illuminate the cornea of the eye and is directed to the cornea's curvature center, by the luminous flux from the light source, and the arithmetic control unit estimates the cornea shape of the eye.

5. An eye characteristic measuring apparatus as set forth in claim 2 or claim 3, wherein the reference reflecting article is formed, at least, by a lens unit having refractive power and a reflecting surface having diffusion function, and at least the reflecting surface is formed as a model eye movable finely, and the arithmetic control unit drives the model eye to be movable finely to remove noise, for example, speckle pattern.

6. An eye characteristic measuring apparatus as set forth in claim 5, wherein the setting data estimated by the arithmetic control unit includes at least rough spherical surface component of the eye to be inspected, and the arithmetic control unit varies a position of the reference reflecting surface or refractive power of the lens unit in response to the setting data.

7. An eye characteristic measuring apparatus as set forth in claim 6, wherein the setting data estimated by the arithmetic control unit further includes the rough astigmatism component of the eye, and in response to this, refractive power of the lens unit is varied.

8. An eye characteristic measuring apparatus as set forth in claim 2 or claim 4, wherein the reference reflecting article is, at least, a reflecting surface having prescribed curvature and is movable in the optical axis direction, and the setting data estimated by the arithmetic control unit includes at least data corresponding to the rough cornea shape of the eye, and the arithmetic control unit varies the position of the reflecting surface in the optical axis direction in response to the setting data.

9. An eye characteristic measuring apparatus as set forth in claim 8, wherein the arithmetic control unit moves the reflecting surface in the optical axis direction in response to the setting data, so that a converging position of the luminous flux of the reference optical system is substantially coincident with the curvature center of the reflecting surface.

10. A eye characteristic measuring apparatus as set forth in claim 9, wherein the setting data estimated by the arithmetic control unit further includes astigmatism component of rough cornea shape of the eye, and the arithmetic control unit various refractive power of the lens unit in response to the setting data.

11. An eye characteristic measuring apparatus as set forth in any one of claims 1 to 4, wherein a plurality of reference reflecting units are prepared, and can be selected in response to the optical characteristics of the eye to be inspected.

12. An eye characteristic measuring apparatus as set forth in any one of claims 1 to 4, wherein the changing unit is constituted by a pair of analyzers arranged for the measurement optical system and the reference optical system, respectively.

13. An eye characteristic measuring apparatus as set forth in any one of claims 1 to 4, wherein the changing unit includes a beam splitter which is constituted by a rhombic prism arranged for the measurement optical system and the reference optical system, respectively.

* * * * *